(12) United States Patent
Braeckmans et al.

(10) Patent No.: US 12,338,423 B2
(45) Date of Patent: Jun. 24, 2025

(54) METHOD AND DEVICE TO PROVIDE A MICROFLUIDIC FLOW

(71) Applicants: UNIVERSITEIT GENT, Ghent (BE); CNRS, Paris (FR); ISEN YNCRÉA HAUTS-DE-FRANCE, Lille (FR); UNIVERSITÉ DE LILLE, Lille (FR); UNIVERSITÉ POLYTECHNIQUE HAUTS-DE-FRANCE, Valenciennes (FR); CENTRALE LILLE INSTITUTE, Villeneuve-d'Ascq (FR)

(72) Inventors: Kevin Braeckmans, Lokeren (BE); Ranhua Xiong, Ghent (BE); Majid Layachi, Lille (FR); Anthony Treizebre, Coutiches (FR); Francois Anquez, Hellemmes (FR); Quentin Thommen, Lille (FR); Emmanuel Courtade, Hellemmes (FR)

(73) Assignees: UNIVERSITEIT GENT, Ghent (BE); CNRS, Paris (FR); ISEN YNCRÉA HAUTS-DE-FRANCE, Lille (FR); UNIVERSITÉ DE LILLE, Lille (FR); UNIVERSITÉ POLYTECHNIQUE HAUTS-DE-FRANCE, Valenciennes (FR); CENTRALE LILLE INSTITUTE, Villeneuve-d'Ascq (FR)

( * ) Notice: Subject to any disclaimer, the term of this patent is extended or adjusted under 35 U.S.C. 154(b) by 904 days.

(21) Appl. No.: 17/607,693

(22) PCT Filed: Apr. 30, 2020

(86) PCT No.: PCT/EP2020/062084
§ 371 (c)(1),
(2) Date: Oct. 29, 2021

(87) PCT Pub. No.: WO2020/221883
PCT Pub. Date: Nov. 5, 2020

(65) Prior Publication Data
US 2022/0228094 A1  Jul. 21, 2022

(30) Foreign Application Priority Data
May 2, 2019  (EP) .................................... 19172343

(51) Int. Cl.
*C12M 3/06* (2006.01)
*C12M 1/00* (2006.01)

(52) U.S. Cl.
CPC ............ *C12M 23/16* (2013.01); *C12M 45/07* (2013.01)

(58) Field of Classification Search
CPC ......... B01L 3/502761; B01L 3/502776; B01L 3/502784; B01L 2200/0636;
(Continued)

(56) References Cited

U.S. PATENT DOCUMENTS 9,139,416 B2   9/2015  Li et al.
9,957,476 B2   5/2018  Gunn-Moore et al.
(Continued)

FOREIGN PATENT DOCUMENTS

EP        2272945 A1    1/2011
WO     2009010719 A1    1/2009

OTHER PUBLICATIONS

Extended European Search Report from European Application No. 19172343.6, Oct. 18, 2019.
(Continued)

*Primary Examiner* — Jill A Warden
*Assistant Examiner* — Dwayne K Handy
(74) *Attorney, Agent, or Firm* — Workman Nydegger (57) ABSTRACT

A method to provide a microfluidic flow comprising a central flow and at least one outer flow, such that the central
(Continued)

flow includes a first material and the at least one outer flow comprises a second material. One of the first material and the second material has cells and the other of the first material and the second material has solid particles. The method involves injection of a first suspension including the first material through a central inlet with a flow rate $Q2$ and injection of a second suspension comprising the second material through a pair of side inlets with a flow rate $Q2$, whereby the ratio of the flow rate $Q2$ over the flow rate $Q1$ is at least 4. A device provides such microfluidic flow and a method is provided to alter biological cells.

10 Claims, 5 Drawing Sheets

(58) Field of Classification Search
CPC ........... B01L 2200/0673; C12M 23/16; C12M 35/08; C12M 45/07
See application file for complete search history.

(56) References Cited

U.S. PATENT DOCUMENTS

| | | |
|---|---|---|
| 2007/0269875 A1 | 11/2007 | Koller et al. |
| 2013/0113140 A1 | 5/2013 | Gunn-Moore et al. |
| 2019/0119624 A1 | 4/2019 | Tandon et al. |

OTHER PUBLICATIONS

International Search Report and Written Opinion from PCT Application No. PCT/EP2020/062084, Jul. 30, 2020.

METHOD AND DEVICE TO PROVIDE A MICROFLUIDIC FLOW

FIELD OF THE INVENTION

The present invention relates to a method and to a device to provide a microfluidic flow comprising a central flow and an outer flow, whereby the central flow comprises a first material and the outer flow comprises a second material, with one of the first material and the second material comprising cells and the other of the first material and the second material comprising solid particles. The invention further relates to a method of altering cells by using such method or such device and to the use of such method and device in methods to manipulate cells.

BACKGROUND ART

Plasmonic nanoparticles are frequently used in all fields of applications including biomedical applications, as for example in cell therapy, immunotherapy, gene therapy and cell transfection. Such biomedical applications all require the intracellular delivery of exogenous compounds into cells. Regardless of the specific application, the common challenge is to overcome the cell membrane, which represents a major obstacle for most macromolecules and nanoparticles.

Physical methods for the delivery of compounds into cells have attracted considerable interest. Such methods have in common that the permeability of the cell membrane is increased, allowing passage of compounds across the cell membrane.

One promising physical method for the delivery of exogenous compounds into cells is photoporation. In photoporation cells are first incubated with plasmonic particles, as for example gold nanoparticles, which adsorb to the cell membrane. By applying laser irradiation localized photothermal effects are produced which result in a transient permeabilization of the membrane. Although photoporation is a promising technique for use in cell therapy, immunotherapy, gene therapy and the production of new cell lines, concerns about the potential toxicity of plasmonic nanoparticles have been raised. Additionally, plasmonic nanoparticles, such as gold nanoparticles, tend to fragment into tiny pieces upon intense laser illumination used in photoporation. Reportedly, such small gold nanoparticles have the potential to be genotoxic when internalized into cells. Considering that the photoporation method requires close contact between the plasmonic nanoparticles and the cells, there is a nanotoxicological concern to use photoporation for example for transfecting cells to be used in cell therapies.

Therefore, to avoid any discussion about the potential toxicity of plasmonic nanoparticles, used for example in cell therapy, immunotherapy and gene therapy, there is a need to provide methods avoiding the direct contact of the plasmonic nanoparticles with the cells during photoporation.

U.S. Pat. No. 9,957,476 describes a system for the poration of cells by using plasmonic nanoparticles. The system uses a laser to create an optical trap so as to position a nanoparticle near the cell and uses a laser directed on the optically trapped particle for causing laser-induced breakdown of the optically trapped particle thus causing poration of the cell. The system has however a limited throughput and does not allow upscaling for treatment of a significant number of cells within a short time span. Consequently, the system is not suitable for use in cell therapy.

U.S. Pat. No. 9,139,416 describes a microfluidic device comprising a substrate having a microchannel whereby the walls of the microchannel are provided with nanowires. Upon irradiation with laser light cells while flowing through the channel can be photoporated. The device does however not allow to tune the distance between the plasmonic structure and the cells as would be needed to maximize the performance of the system, especially when dealing with different cell types. Furthermore the device suffers from damage of the nanowires and thus has a limited life time.

EP2272945 describes a method to porate cells by placing a cell at or near a surface of a substrate provided with surface structures coated with a metal (gold) and by irradiating the surface of the substrate with a laser pulse. Such method has the disadvantage that the cell membrane is permeabilizes at one side, i.e. the side where the cells are in contact with the surface structures of the substrate (the bottom side of the cells), while the compounds that need to be delivered into the cells are present primarily at the opposite side (the upper side of the cells). As a result the delivery efficiency is low, especially for large molecules.

SUMMARY OF THE INVENTION

It is an object of the present invention to provide a method to provide a microfluidic flow comprising a first material and a second material, whereby direct contact between the first and second material in the microfluidic flow is avoided. In particular it is an object to provide a microfluidic flow comprising biological cells and solid particles such as nanoparticles and/or microparticles, whereby direct contact between the biological cells and the solid particles is avoided.

It is another object of the present invention to provide a method to provide a microfluidic flow, whereby the first material and the second material, for example biological cells and nanoparticles and/or microparticles, are transported in the microfluidic flow at a predetermined minimal distance from each other.

It is another object to provide a device to provide a microfluidic flow comprising a central flow comprising the first material and at least one outer flow comprising the second material, for example a central flow comprising biological cells and an outer flow comprising nanoparticles and/or microparticles.

It is also an object to provide a method allowing to alter biological cells not requiring close or direct contact between biological cells and nanoparticles and/or microparticles.

It is a further object of the present invention to provide a method to alter, treat or manipulate biological cells, in particular suitable for drug delivery, cell therapy, immunotherapy, gene therapy and transfection of cells.

It is a further object of the invention to provide a method to alter, treat or manipulate biological cells in high throughput, for example to provide a method to photoporate biological cells in high throughput.

It is a further object of the invention to provide a method that allows continuous replenishing of nanoparticles and/or microparticles (which are typically damaged upon laser irradiation), ensuring continuous operation of a microfluidic device and thus ensuring a continuous manipulation of biological cells, for example a continuous photoporation of biological cells.

According to a first aspect of the present invention a method to provide a microfluidic flow comprising a first material and a second material is provided. The microfluidic flow comprises a central flow and at least one outer flow surrounding or flanking the central flow, with the central flow comprising the first material and being free or substantially free of the second material and with the at least one outer flow comprising the second material and being free or substantially free of the first material. One of the first material and the second material comprises cells. The other of the first material and the second material comprises solid particles selected from the group of nanoparticles, microparticles and combinations of nanoparticles and/or microparticles. The method comprises the steps of
- providing a first suspension comprising the first material and being free of the second material;
- providing a second suspension comprising the second material and being free of the first material;
- injecting the first suspension with a flow rate Q1 through a central inlet oriented along axis A1 to provide a flow of the first suspension. The flow of the first suspension is thereby preferably oriented along the axis A1;
- injecting the second suspension with a flow rate Q2 to a first junction region of the flow of the first suspension through a first pair of side inlets to provide the microfluidic flow. The first pair of side inlets comprises a first side inlet oriented along axis A2' and a second side inlet oriented along axis A2". The axis A1 and the axis A2' define an included angle α and the axis A1 and the axis A2" define an included angle α', with the angles α and α' ranging between 10 and 80 degrees. The flow rate Q1 and the flow rate Q2 are adjusted by means to adjust the flow rate Q1 and/or by means to adjust the flow rate Q2 in order to have a ratio of the flow rate Q2 over the flow rate Q1 (referred to as Q2/Q1) of at least 4.

The flow rate Q1 and the flow rate Q2 are preferably adjusted to have a ratio of the flow rate Q2 over the flow rate Q1, Q2/Q1, of at least 8, at least 10, at least 20, at least 50 or at least 100. The microfluidic flow is preferably oriented along axis A1.

The method according to the present invention allows to obtain a microfluidic flow comprising a central flow comprising the first material (and being free or substantially free of the second material) and at least one, preferably one, outer flow surrounding or flanking the central flow. The at least one outer flow comprises the second material (and is free or substantially free of the first material).

The microfluidic flow flows through a microfluidic flow channel having a radius or equivalent radius W. The microfluidic channel has preferably a radius or equivalent radius W ranging between 10 µm and 200 µm, for example between 10 µm and 100 µm, as for example 50 µm.

The microfluidic flow channel may have any type of cross-section as for example a circular, elliptical or polygonal (preferably square or rectangular) cross-section.

In preferred methods the first material comprises cells while the second material comprises solid particles such as for example nanoparticles, microparticles or a combination of nanoparticles and/or microparticles.

In alternative preferred methods the second material comprises cells while the first material comprises solid particles as for example nanoparticles, microparticles or a combination of nanoparticles and/or microparticles.

The method according to the present invention allows to control the distance between the first material and the second material in the microfluidic flow. In particular the method allows to control the distance between cells and solid particles. The method according to the present invention allows for example to obtain a microfluidic flow comprising biological cells and solid particles such as nanoparticles, microparticles or a combination of nanoparticles and/or microparticles whereby the solid particles are situated at close distance from the cells but whereby the solid particles are not contacting the cells.

In particular, the distance d between the first material and the second material in the microfluidic flow ranges between 0.01 µm and 500 µm. Even more preferably, the distance d between the first material and the second material ranges between 0.05 µm and 20 µm or between 0.1 µm and 1 µm.

In case the first material comprises cells while the second material comprises solid particles, the distance d between the biological cells and the solid particles is preferably at least 0.01 µm, more preferably at least 0.1 µm, at least 1 µm, at least 5 µm, at least 10 µm or at least 50 µm.

For the application to alter cells, for example to permeabilize cells, the distance d between the cells and the solid particles such as nanoparticles, microparticles or a combination of nanoparticles and/or microparticles ranges preferably between 0.01 µm and 500 µm. More preferably, for the application to alter cells, for example to permeablize cells, the distance d between the biological cells and the solid particles ranges between 0.1 µm and 50 µm, for example between 5 µm and 20 µm.

The method according to the present invention allows to adjust the position of the first material and the second material in the microfluidic flow and in particular the position of the first material relative to the second material, for example by changing the orientation of the axis A1 and/or the orientation of the axis A2' and/or the axis A2". More preferably, the microfluidic flow and in particular the (relative) position of the first material and the second material in the microfluidic flow is influenced by changing the orientation of the axes A2' and/or A2" relative to the orientation of the axis A1, for example by changing the angle α and/or the angle α'.

The microfluidic flow and in particular the (relative) position of the first material and the second material in the microfluidic flow can be adjusted by changing the flow rate Q1 and/or the flow rate Q2. More preferably, the microfluidic flow and in particular the (relative) position of the first material and the second material in the microfluidic flow is influenced by changing the ratio of the flow rate Q2 and the flow rate Q1, i.e. the ratio Q2/Q1.

Furthermore the flow rates Q1 and Q2 has to adjusted to ensure cell viability.

Although Applicant does not want to be bound by any theory, the ratio Q2/Q1 is preferably larger than $$\frac{2 \cdot \mu \cdot V_m}{l \cdot \tau_{max}}$$

with µ: the dynamic viscosity of the flow;
V$_m$: the velocity of the flow;
l: the width of the microfluidic channel; and
τ$_{max}$: the maximal shear stress.

A typical microfluidic flow having a dynamic viscosity of $10^{-3}$ Pa·s, a velocity of V 1 m/s, a radius of the microfluidic channel of 50 µm and a maximal shear stress τ$_{max}$ of 20 Pa ensuring cell viability leads to a ratio Q2/Q1 of at least 4.

Preferably, the microfluidic flow and in particular the (relative) position of the first material and the second material in the microfluidic flow are adjusted by changing the orientation of the axes A2' relative to the orientation of the axis A1 and/or the orientation of the axis A2" relative to the orientation of the axis A1 and by changing the ratio Q2/Q1.

The angles α and α' can be chosen independently from each other between 10 and 80 degrees, more preferably between 30 and 60 degrees, for example between 40 and 50 degrees as for example 45 degrees. The angles α and α' can be equal or not equal. In preferred embodiments the angles α and α' are equal.

In preferred embodiments the axis A1, the axis A2' and the axis A2" are oriented in a plane, referred to as plane PH. More preferably, the axis A1, the axis A2' and the axis A2" are oriented in the plane PH and the angles α and α' are equal.

The flow rate Q1 ranges preferably between $10^{-7}$ mL/s and 100 mL/s and more preferably between $10^{-6}$ mL/s and 10 mL/s as for example $10^{-4}$ mL/s or $10^{-3}$ mL/s.

The flow rate Q2 ranges preferably between $10^{-6}$ mL/s and 1000 mL/s and more preferably between $10^{-5}$ mL/s and 100 mL/s as for example $10^{-3}$ mL/s or $10^{-2}$ mL/s.

For the application of the microfluidic flow to alter cells, for example to permeabilize cells, the flow rate Q1 ranges preferably between $10^{-7}$ mL/s and 1.6 mL/s, more preferably the flow rate Q1 ranges between $10^{-4}$ mL/s and 0.4 mL/s. The flow rate Q2 ranges preferably between $10^{-6}$ mL/s and 2 mL/s.

For the application of the microfluidic flow to alter cells, for example to permeabilize cells, the first suspension preferably comprises the cells and the second suspension preferably comprises the solid particles as for example nanoparticles, microparticles or a combination of nanoparticles and/or microparticles. However, also methods whereby the second suspension comprises the cells and the first suspension comprises the solid particles, as for example nanoparticles, microparticles or a combination of nanoparticles and/or microparticles can be considered as well.

The flow rate Q2 of the second suspension through the first side inlet is preferably equal to the flow rate Q2 of the second suspension through the second side inlet. Alternatively, the flow rate of the second suspension through the first side inlet and the flow rate of the second suspension through the second side inlet are not equal. In such case the flow rate of the second suspension through the first side inlet is referred to as Q2' and the flow rate of the second suspension through the second side inlet is referred to as Q2". The flow rate Q2 is then defined as the average of Q2' and Q2".

The microfluidic flow preferably comprises a central flow and one outer flow surrounding or flanking the central flow. For the purpose of this invention the term 'surrounding' refers to enclosing on all sides or enveloping. The term 'flanking' refers to being situated at the side of.

The microfluidic flow comprises for example a central flow and an peripheral outer flow surrounding the central flow. Alternatively, the microfluidic flow comprises a central flow and one outer flow flanking the central flow. In particular embodiments the microfluidic flow comprises a central flow and more than one outer flow, for example a first outer flow formed by the injection of the second suspension by the first side inlet and a second outer flow formed by the injection of the second suspension by the second side inlet. The first and the second outer flow are thereby both flanking the central flow. The first outer flow and the second outer flow are for example flanking the central flow at opposite sides of the central flow. It is clear that the microfluidic flow provided by the method according to the present invention may comprise more than two outer flows.

The concentration of cells in the first suspension or in the second suspension ranges preferably between $10^2$ and $10^9$ per millilitre and more preferably between $10^3$ and $10^8$ per millilitre as for example between $10^4$ and $10^7$ per millilitre in order to obtain a high throughput.

The cells are preferably present in a cell medium or a suitable solution, in particular a suitable transfection buffer solution.

Preferably, the solid particles do not dissolve in the suspension. Preferably, the solid particles are clearly distinguishable in the suspension.

Preferred solid particles, as for example nanoparticles, microparticles or a combination of nanoparticles and/or microparticles, are particles that are able to absorb electromagnetic radiation such as to generate a vapour bubble, for example a vapour microbubble or a vapour nanobubble, in or from a surrounding medium.

The solid particles preferably comprise metal nanoparticles or microparticles, metal oxide nanoparticles or microparticles, carbon or carbon based nanoparticles or micoparticles, particles comprising one or more light absorbing compounds or particles loaded or functionalized with one or more light absorbing compounds.

Examples of metal nanoparticles or microparticles comprise gold particles, silver particles, platinum particles, palladium particles, copper particles and alloys thereof. Preferred metal nanoparticles of microparticles comprise gold particles, silver particles and alloys thereof.

Examples of metal oxide nanoparticles or microparticles comprise iron oxide, titanium oxide, zirconium oxide, cerium oxide, zinc oxide and magnesium oxide.

Examples of carbon or carbon based nanoparticles or microparticles comprise graphene quantum dots, (reduced) graphene oxide and carbon nanotubes.

Examples of particles comprising one or more light absorbing compounds or particles loaded or functionalized with one or more light absorbing compounds comprise particles comprising, loaded or functionalized with synthetic organic or inorganic absorbers as well as particles comprising, loaded or functionalized with naturally occurring absorbers or derivatives thereof. Particular examples comprise liposomes, solid lipid nanoparticles, polymer based particles comprising loaded or functionalized with light absorbing dye molecules such as indocyanine green, quantum dots with a good photothermal conversion efficiency, naturally occurring light absorbers like pigments (such as melanin, rhodopsin, photopsins or iodopsin) and synthetic analogs like polydopamine, or photosensitizers used in photodynamic therapy.

The solid particles may comprise a combination of particles, i.e. a combination of nanoparticles and/or microparticles as for example a combination of nanoparticles, a combination of microparticles or a combination of nanoparticles and nanoparticles.

Preferred combinations of particles comprise groups or clusters of microparticles, groups or clusters of nanoparticles or groups or clusters of nanoparticles and microparticles.

A particularly preferred combination of solid particles comprises nanobombs as described in patent application EP 18213548.3, hereby incorporated by reference. Such nanobombs typically comprise at least one particle of a first type surrounded by at least one particle of a second type. The at least one particle of the first type preferably comprises a particle that is able to absorb electromagnetic radiation and is able to generate a vapour bubble in or from a surrounding medium upon irradiation. The at least one particle of the second type is preferably in close proximity to the at least one particle of the first type. The at least one particle of the second type is adapted to be propelled away from the particle of the first type by the generation of the vapour bubble. The at least one particle of the second type is preferably adapted to alter a cell, for example to permeabilize a cell, once propelled upon the generation of the vapour bubble. The particle or particles of the first type thus generate a vapour bubble whereas the particle or particles of the second type functions as a nanoprojectile to alter a cell, for example to permeabilize a cell. For the purpose of this invention the term 'in close proximity to' is defined as either being in contact with or being positioned at a distance d smaller than 1 μm, with the distance d being the closest distance between the outer surface of a particle of the first type and the outer surface of a particle of the second type. For the purpose of this invention the term 'in close proximity to' or 'being in close proximity to' is used with reference to neighbouring or surrounding particles. The at least one particle of the first type of a nanobomb comprises for example nanoparticles and/or microparticles as described above. Particularly preferred particles of the first type are gold particles, carbon or carbon based particles or iron oxide particles. The at least one particle of the second type of a nanobomb comprises for example polymer particles (for example polystyrene beads or poly(lactic-co-glycolic acid) (PLGA) beads), metal oxide particles (for example titania or zirconia particles, silicon or silicon oxide particles (micro or nanoparticles), liposomes, drug loaded polymer particles, drug loaded metal oxide particles, drug loaded silicon or silicon particles and drug loaded liposomes.

The concentration of solid particles as for example nanoparticles, microparticles or a combination of nanoparticles and/or microparticles in the first suspension or in the second suspension ranges preferably between $10^3$ and $10^9$ per milliliter.

For the application of the microfluidic flow to alter cells, for example to permeabilize, the concentration of solid particles ranges preferably between $10^3$ and $10^8$ per millilitre as for example between $10^4$ and $10^6$ per millilitre to balance efficient permeablilization with cell viability.

The solid particles are preferably present in cell medium or a suitable solution in which the solid particles have sufficient colloidal stability, for example a suitable transfection buffer solution.

In a first preferred group of methods the first suspension comprises biological cells and the second suspension comprises solid particles, as for example nanoparticles, microparticles or a combination of nanoparticles and/or microparticles, resulting in a microfluidic flow comprising a central flow of biological cells surrounded by an outer flow of solid particles. Preferably, the biological cells and the solid particles in the microfluidic flow are not contacting each other.

In a second group of methods, the first suspension comprises solid particles as for example nanoparticles, microparticles or a combination of nanoparticles and/or microparticles and the second suspension comprises biological cells, resulting in a microfluidic flow comprising a central flow of solid particles surrounded by an outer flow of biological cells. Preferably, the nanoparticles and/or microparticles and the biological cells in the microfluidic flow are not contacting each other.

In preferred methods according to the present invention, the method further comprises the step of
injecting a fluid, for example a buffer solution, to the microfluidic flow, preferably to the first junction region, through at least one additional inlet and preferably through a pair of additional inlets. The fluid is injected with a flow rate Q3.

The additional inlet or inlets is/are preferably oriented along axis A3, having an orientation different from the orientation of any of the axis A1, A2' and A2". The injected fluid is preferably free of said first particles and said second particles.

The fluid is preferably injected to the first junction region, however injection of the fluid to any junction region downstream the first junction region can also be considered.

In case the fluid is injected through a pair of additional inlets, the pair of additional inlets comprises a first additional inlet and a second additional inlet, both oriented along axis A3 to inject the fluid in opposite directions to the first junction region or to a further junction region.

By the additional step of injecting a fluid, for example a buffer solution, to the microfluidic flow, the microfluidic flow and in particular the relative position of the first material to the second material, i.e. between the cells and the solid particles, in the microfluidic flow can be further optimized.

By adjusting the orientation of the axis A3, in particular the orientation of the axis A3 relative to the axis A1, and/or by adjusting the flow rate Q3 (for example the flow rate Q3 relative to the flow rate Q1 or relative to the flow rate Q2), the microfluidic flow and in particular the central flow and the at least one outer flow, and more particularly the relative position of the first material to the second material, i.e. the relative position of the cells to the solid particles, can be influenced.

In preferred embodiments the axis A1, the axis A2' and the axis A2" are oriented in a plane, referred to as plane PH whereas the axis A3 is not oriented in the plane PH.

In a particular preferred embodiment the axis A1, the axis A2' and the axis A2' are oriented in a plane PH and the axis A3 is oriented perpendicular or substantially perpendicular to the plane PH.

Preferably, the flow rate Q3 ranges between the flow rate Q2 divided by 100 (Q2/100) and the flow rate Q2 multiplied with 100 (Q2×100). More preferably, the flow rate Q3 ranges between the flow rate Q2 divided by 10 (Q2/10) and the flow rate Q2 multiplied with 10 (Q2×10).

The fluid preferably comprises distilled water, cell medium or a buffer solution.

The method according to the present invention may further comprise one or more additional injections of the second suspension. In such case the method according to the present invention comprises the additional step of
injecting the second suspension with a flow rate Q4 to the first junction region or to a second junction region of the flow of the microfluidic flow through a second pair of side inlets to provide the microfluidic flow. The second junction region, if present, is positioned downstream the first junction region. The second pair of side inlets comprises a first side inlet oriented along axis A4' and a second side inlet oriented along axis A4". The axes A1 and said axes A4' define an included angle β and the axes A1 and the axes A4" define an included angle β', with the angles β and β' ranging between 10 and 80 degrees.

Possibly, the method further comprises the step or steps of injection the second suspension through a further pair of side inlets or through further pairs of side inlets, for example through a third pair of side inlets or through a third and a fourth pair of side inlets.

By the additional injection step or steps of the second suspension, the microfluidic flow and in particular the relative position of the first material to the second material in the microfluidic flow can be further optimized.

The microfluidic flow and in particular the (relative) position of the first material and the second material in the microfluidic flow can be (further) adjusted in the method according to the present invention for example by changing the orientation of the axis A4' and/or the axis A4". More preferably, the microfluidic flow and in particular the (relative) position of the first material and the second material in the microfluidic flow is influenced by changing the orientation of the axes A4' relative to the axis A1 and/or the orientation of axis A4" relative to the axis A1, for example by changing the angle β and/or the angle β'.

The microfluidic flow and in particular the (relative) position of the first material and the second material in the microfluidic flow can be (further) adjusted by changing the flow rate Q4. More preferably, the microfluidic flow and in particular the (relative) position of the first material and the second material in the microfluidic flow is influenced by changing the ratio of the flow rates Q4 and the flow rate Q1, i.e. the ratio Q4/Q1.

Preferably, the microfluidic flow and in particular the (relative) position of the first material and the second material in the microfluidic flow are (further) adjusted by changing the orientation of the axes A4' relative to the orientation of the axis A1 and/or the orientation of the axis A4" relative to the orientation of the axis A1 and by changing the ratio Q4/Q1.

The angles β and β' can be chosen independently from each other between 10 and 80 degrees, more preferably between 30 and 60 degrees, for example between 40 and 50 degrees as for example 45 degrees. The angles β and β' can be equal or not equal. In preferred embodiments the angles β and β' are equal.

In preferred embodiments the axis A1, the axis A4' and the axis A4" are oriented in a plane PH2. Preferably, the axis A3 is not oriented in the plane PH2.

In a particular preferred embodiment the axis A1, the axis A2', the axis A2", the axis A4' and the axis A4" are oriented in one plane, referred to as the plane PH, while the axis A3 is not oriented in the plane PH. Even more preferably, the axis A1, the axis A2', the axis A2", the axis A4' and the axis A4" are oriented in the plane PH while the axis A3 is oriented perpendicular or substantially perpendicular to the plane PH.

The flow rate Q4 ranges preferably between $10^{-6}$ mL/s and 1000 mL/s and more preferably between $10^{-5}$ mL/s and 100 mL/s as for example $10^{-3}$ mL/s or $10^{-2}$ mL/s. Preferably, the flow rate Q4 is equal or substantially equal to the flow rate Q3.

According to a second aspect of the present invention a device for providing a microfluidic flow comprising a first material and a second material is provided. The microfluidic flow comprises a central flow and at least one outer flow surrounding or flanking the central flow. The central flow comprises the first material and is substantially free of the second material and the at least one outer flow comprises the second material and is substantially free of the first material. The device is suitable to provide a microfluidic flow whereby one of the first material and the second material comprises cells and the other of the first material and the second material comprises solid particles selected from the group of nanoparticles, microparticles and combinations of nanoparticles and/or microparticles.

The first material comprises for example biological cells whereas the second material comprises solid particles. Alternatively, the second material comprises biological cells whereas the first material comprises solid particles.

For some applications, as for example applications to alter biological cell, the solid particles are preferably particles that are able to absorb electromagnetic radiation. Particularly preferred solid particles comprise nanobombs as described above.

The device comprises
- a central inlet oriented along axis A1 for injecting a first suspension comprising the first material and being free of the second material with a flow rate Q1 to provide a flow of the first suspension. The flow of the first suspension is preferably oriented along said axis A1;
- a first pair of side inlets for injecting a second suspension comprising the second material and being free of the first material with a flow rate Q2 to a first junction region of the flow of the first suspension. The first pair of side inlets comprise a first side inlet oriented along axis A2' and a second side inlet oriented along axis A2". The axis A1 and the axis A2' define an included angle α and the axis A1 and the axis A2" define an included angle α'. The angle α and a' range between 10 and 80 degrees;
- means to adjust the flow rate Q1 and/or means to adjust the flow rate Q2 to obtain a ratio of the flow rate Q1 to the flow rate Q2 (referred to as Q2/Q1) being higher than 4, for example higher than 8, higher than 10, higher than 50 or higher than 100.

The microfluidic flow flows through a microfluidic flow channel having a radius or equivalent radius W. The microfluidic channel has preferably a radius or equivalent radius W ranging between 10 μm and 200 μm, for example between 10 μm and 100 μm, as for example 50 μm.

The microfluidic flow channel may have any type of cross-section as for example a circular, elliptical or polygonal (preferably square or rectangular) cross-section.

In preferred embodiments, the device further comprises at least one additional inlet, preferably a pair of additional inlets, for injecting a fluid, for example a buffer solution, with a flow rate Q3 to said first junction region. The at least one additional inlet is preferably oriented along axis A3 having an orientation different from the orientation of any of the axes A1, A2' and A2".

The additional inlet or additional inlets are preferably injecting the fluid, for example the buffer solution, to the first junction region, however injection of the fluid, for example the buffer solution, to a junction region downstream the first junction region can also be considered.

Optionally, the device according to the present invention further comprises means to adjust the flow rate Q3.

The device may comprise a pair of additional inlets comprising a first additional inlet and a second additional inlet. In such case, the first and second additional inlets are preferably oriented along axis A3 and are injecting the fluid, for example the buffer solution, in opposite directions to the first junction region or to a further junction region.

The device may comprise a central chamber, whereby the central inlet is injecting the first suspension to the central chamber, the side inlets are injection the second suspension to the central chamber and the additional inlet or inlets are injecting a fluid, for example a buffer solution, to the central chamber. The central chamber has preferably an outlet for providing the microfluidic flow.

In particularly preferred embodiments the device further comprises a second pair of side inlets, and possibly further pair(s) of side inlets, for injecting the second suspension with a flow rate Q4 to the first junction region or to a second junction region of the microfluidic flow. The second junction region, if present, is positioned downstream the first junction region. The second pair of side inlets comprises a first side inlet oriented along axis A4' and a second side inlet oriented along axis A4". The axes A1 and said axes A4' define an included angle β and the axes A1 and the axes A4" define an included angle β', with the angles β and β' ranging between 10 and 80 degrees.

Optionally, the device according to the present invention comprises means to adjust the flow rate Q4. The flow rate Q4 is preferably equal or substantially equal to the flow rate Q2.

According to a third aspect of the present invention a method to alter biological cells is provided. The method is for example an ex vivo or in vitro method. The method to alter biological cells preferably comprises the steps of providing a microfluidic flow according to the above described method to provide a microfluidic flow comprising a first material and a second material, with one of the first material and the second material comprising cells and the other of the first and the second material comprising solid particles selected from the group of nanoparticles, microparticles and combinations of nanoparticles and/or microparticles. The microfluidic flow comprises a central flow and at least one outer flow surrounding or flanking the central flow. The central flow comprises the first material and is free or substantially free of the second material and the at least one outer flow comprises the second material and is free or substantially free of the first material;

irradiating said microfluidic flow with electromagnetic radiation.

The microfluidic flow is preferably obtained by using the above described method to provide a microfluidic flow and/or by using the above describe device for providing a microfluidic flow.

Preferably, the solid particles are able to absorb electromagnetic radiation such as to generate a vapour bubble, for example a vapour microbubble or a vapour nanobubble, in or from a surrounding medium. Preferred solid particles comprise nanoparticles or microparticles able to absorb electromagnetic radiation or a combination of such nanoparticles and/microparticles.

A preferred method to alter biological cells comprises the steps of providing a microfluidic flow according to the above described method to provide a microfluidic flow comprising a first material and a second material, with one of the first material and the second material comprising cells and the other of the first material or the second material comprising solid particles able to absorb electromagnetic radiation. The microfluidic flow comprises a central flow and at least one outer flow surrounding or flanking the central flow. The central flow comprises the first material and is free or substantially free of the second material and the at least one outer flow comprises the second material and is free or substantially free of the first material;

irradiating said microfluidic flow with electromagnetic radiation.

Preferably, the first material comprises cells and the second material comprises particles able to absorb electromagnetic radiation although methods whereby the second material comprises cells and the first material comprises particles able to absorb electromagnetic radiation are not excluded. In a particularly preferred method to alter cells, the first material comprises cells and the second material comprise nanobombs as described above.

By irradiating the microfluidic flow, in particular the particles able to absorb electromagnetic radiation, for example the solid particles, are optically activated. Upon absorption of the electromagnetic radiation by the particles able to absorb electromagnetic radiation, for example the solid particles, local heating is induced resulting in the generation of a vapour bubble, for example a vapour microbubble or a vapour nanobubble. By the generation of a vapour bubble local high-pressure waves are induced which may alter a nearby cell, as for example a biological barrier of a nearby cell. Biological barriers include but are not limited to cellular membranes or barriers as for example cell membranes or cell walls of eukaryotic and prokaryotic cells, intracellular membrane, such as endosomal membranes, nuclear envelopes, mitochondrial membranes.

The terms 'alter', 'altering' or 'alteration' refer to any way to change one or more properties of a cell, for example at least locally. In particular the terms 'alter', 'altering' or 'alteration' refer to any way to change one or more properties of a biological barrier of a cell. Altering includes but is not limited to inducing a local change in a cell's composition, for example in biological barrier's composition by adding, removing, destroying or reorganizing constituents. Altering comprises for example changing one or more physicochemical properties, such as its viscosity, porosity, density, rigidity, elasticity etc. Altering also includes local destruction or rearrangement of barrier constituents, resulting in a change of the composition and/or physicochemical properties of the barrier. Altering includes amongst other deforming, permeabilizing and perforating.

The terms 'deform', 'deforming' and 'deformation' refer to any way to alter the spatial organization or structure of a cell, in particular of a biological barrier of a cell at least partially, for example at least locally. Examples of deforming comprise providing a biological barrier with indentations or invaginations.

The terms 'permeabilize', 'permeabilizing' and 'permeabilization' refer to any way to alter the permeability of a cell, in particular of the permeability of a biological barrier of a cell, at least partially, for example at least locally. Examples of permeabilizing comprise altering the barrier composition or structure so that it becomes more permeable to one or more types of molecules, particles or nanoparticles.

The terms 'perforate', 'perforating' or 'perforation' refer to any way to provide a cell, in particular a biological barrier of a cell, at least partially, for example at least locally, with one or more openings, holes or pores. By perforating a biological barrier, openings are created into the barrier allowing the transport of compounds, such as molecules, particles or nanoparticles, across or into that barrier.

For the purpose of this invention the terms 'perforate', 'perforating', 'perforation' and the terms 'permeabilize', 'permeabilizing', 'permeabilization' are interchangeably used. Similarly, for the purpose of this invention the terms 'opening', 'hole' and 'pore' are interchangeably used.

The microfluidic flow, in particular the particles able to absorb electromagnetic radiation, flow, is preferably irradiated by a pulsed radiation source, although irradiation by a continuous wave radiation source can also be considered. The microfluidic flow of the microfluidic flow can be irradiated by one or more pulses.

When a pulsed radiation source is used, the pulses preferably have a duration in the range of 10 ns down to 0.1 ns or 10 fs.

The fluence (electromagnetic energy delivered per unit area) per pulse of the radiation source ranges preferably between 0.01 and 10 $J/cm^2$, more preferably between 0.05 and 2 $J/cm^2$ as for example 0.5 $J/cm^2$.

The wavelength of the radiation source may range from the ultraviolet region to the infrared region. In preferred methods, the wavelength range of the radiation used is in the visible to the near infrared region.

The method to alter cells according to the present invention is suitable to alter, manipulate and treat cells. The method is in particular suitable to perforate or permeabilize cells in particular biological membranes. By the method transient pores can be formed into membranes allowing the delivering of compounds in the cells or to release compounds from the cell, or to induce cell death.

An important advantage of the method according to the present invention is that the method does not require direct contact between the particles, for example the nanoparticles, microparticles or the combination of nanoparticles and/or microparticles and the biological cells to be altered, deformed, permeabilized or perforated. Consequently, potential risks due to potential toxicity of nanoparticles or microparticles is avoided.

The method according to the present invention is in particular suitable for use in drug delivery, in intracellular delivery of compounds, in cell therapy, in immunotherapy, in gene therapy and in transfection of cells for example stem cells or T cells.

In particular the method is suitable for use in intracellular delivery of nucleic acids, including oligonucleotides, siRNA, mRNA or pDNA.

The method is also suitable for use in the intracellular delivery of nucleoproteins, including ribonucleoproteins, such as Cas9/gRNA.

Furthermore, the method is suitable for use in the intracellular delivery of peptides and proteins, such as nanobodies or antibodies.

In addition, the method is suitable for use in the intracellular delivery of contrast agents, such as quantum dots, iron oxide nanoparticles and gadolinium chelates.

The method is furthermore suitable for use in the intracellular delivery of plasmonic nanoparticles for example for sensing and characterization purposes as for example LSPR sensors (localized surface plasmon resonance) or for SERS (surface enhanced raman spectroscopy).

The method to alter cells according to the present invention has the advantage that the biological cells can be altered without requiring direct contact between the biological cells and the nanoparticles and/or microparticles.

The method furthermore allows to alter, treat or manipulate cells with high throughput. The method allow continuous replenishing of nanoparticles and/or microparticles which are typically damaged during irradiation.

BRIEF DESCRIPTION OF THE DRAWINGS

The present invention will be discussed in more detail below, with reference to the attached drawings, in which:

FIG. 2, comprising FIGS. 2a to 2c.

FIG. 3, comprising

FIG. 4, comprising

BRIEF DESCRIPTION OF THE PREFERRED EMBODIMENTS

The present invention will be described with respect to particular embodiments and with reference to certain drawings, but the invention is not limited thereto but only by the claims. The drawings are only schematic and are non-limiting. The size of some of the elements in the drawing may be exaggerated and not drawn on scale for illustrative purposes. The dimensions and the relative dimensions do not correspond to actual reductions to practice of the invention.

When referring to the endpoints of a range, the endpoints values of the range are included.

When describing the invention, the terms used are construed in accordance with the following definitions, unless indicated otherwise.

The terms 'first', 'second' and the like used in the description as well as in the claims, are used to distinguish between similar elements and not necessarily describe a sequence, either temporally, spatially, in ranking or in any other manner. It is to be understood that the terms so used are interchangeable under appropriate circumstances and that the embodiments of the invention described herein are capable of operation in other sequences than described or illustrated herein.

The term 'and/or' when listing two or more items, means that any one of the listed items can by employed by itself or that any combination of two or more of the listed items can be employed.

The term 'cell' refers to all types of biological cells, including eukaryotic cells and prokaryotic cells. For the purpose of this invention the terms 'cells' and 'biological cells' are interchangeably used.

The term 'microparticle' refers to particles having dimensions (more particularly the smallest dimensions of the particles) ranging between 0.1 µm and 100 µm. The term 'nanoparticle' refers to particles having dimensions (smallest dimensions of the particles) between 1 nm and 100 nm.

The term 'generation of a vapour bubble' includes either expansion of the vapour bubble, either collapse of the vapour bubble or a combination of expansion and collapse of the vapour bubble and secondary effects that can be the result of the bubble expansion and collapse, such as pressure waves and flow of the surrounding medium.

The term 'vapour bubble' or 'bubble' refers to vapour nanobubbles and vapour microbubbles. Preferably, the term 'vapour bubble' or 'bubble' refers to vapour bubbles having a diameter in the range of 10 nm to 100 µm. Vapour bubbles comprise water vapour bubbles, although embodiments are not limited thereto.

Figure 1:
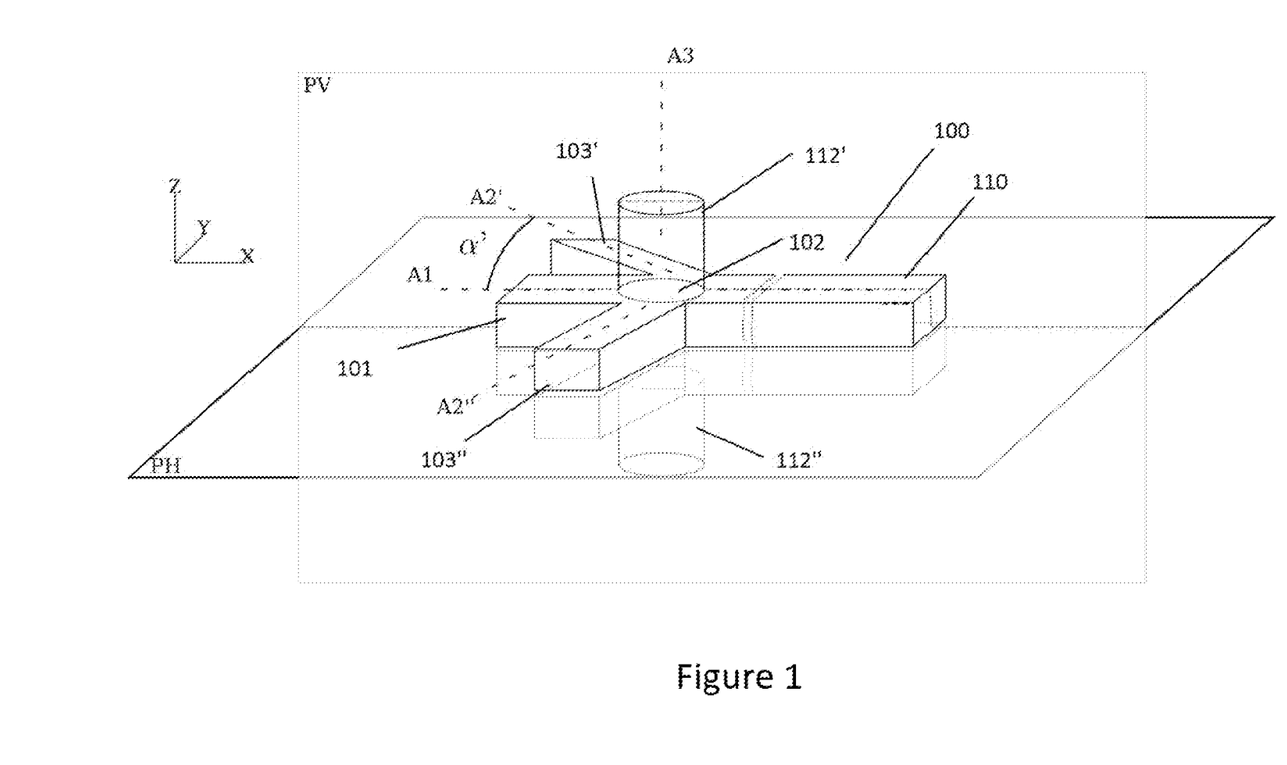
FIG. 1 shows a schematic illustration of a microfluidic device according to the present invention.

FIG. 1 is a schematic illustration of a microfluidic device 100 according to the present invention. The microfluidic device 100 comprises a central inlet 101 oriented along axis A1 for injecting a first suspension with a flow rate Q1 to provide a flow of a first suspension;

a first pair of side inlets 103', 103" for injecting a second suspension with a flow rate Q2 to a first junction region 102 of the flow of the first suspension. The pair of side inlets 103', 103" comprises a first side inlet 103' oriented along axis A2' and a second side inlet 103" oriented along axis A2";

means to adjust the flow rate Q1 (not shown) and/or means to adjust the flow rate Q2 (not shown) to obtain a ratio of the flow rate Q2 to the flow rate Q1 (Q2/Q1) being higher than 4.

The microfluidic device 100 further comprises an outlet 110, preferably oriented along axis A1, for providing the microfluidic flow.

The microfluidic device 100 is adapted to provide a microfluidic flow comprising a first material and a second material whereby the microfluidic flow comprises a central flow comprising the first material and being substantially free of the second material and at least one outer flow surrounding or flanking the central flow comprising the second material and being substantially free of the first material.

Figure 2:
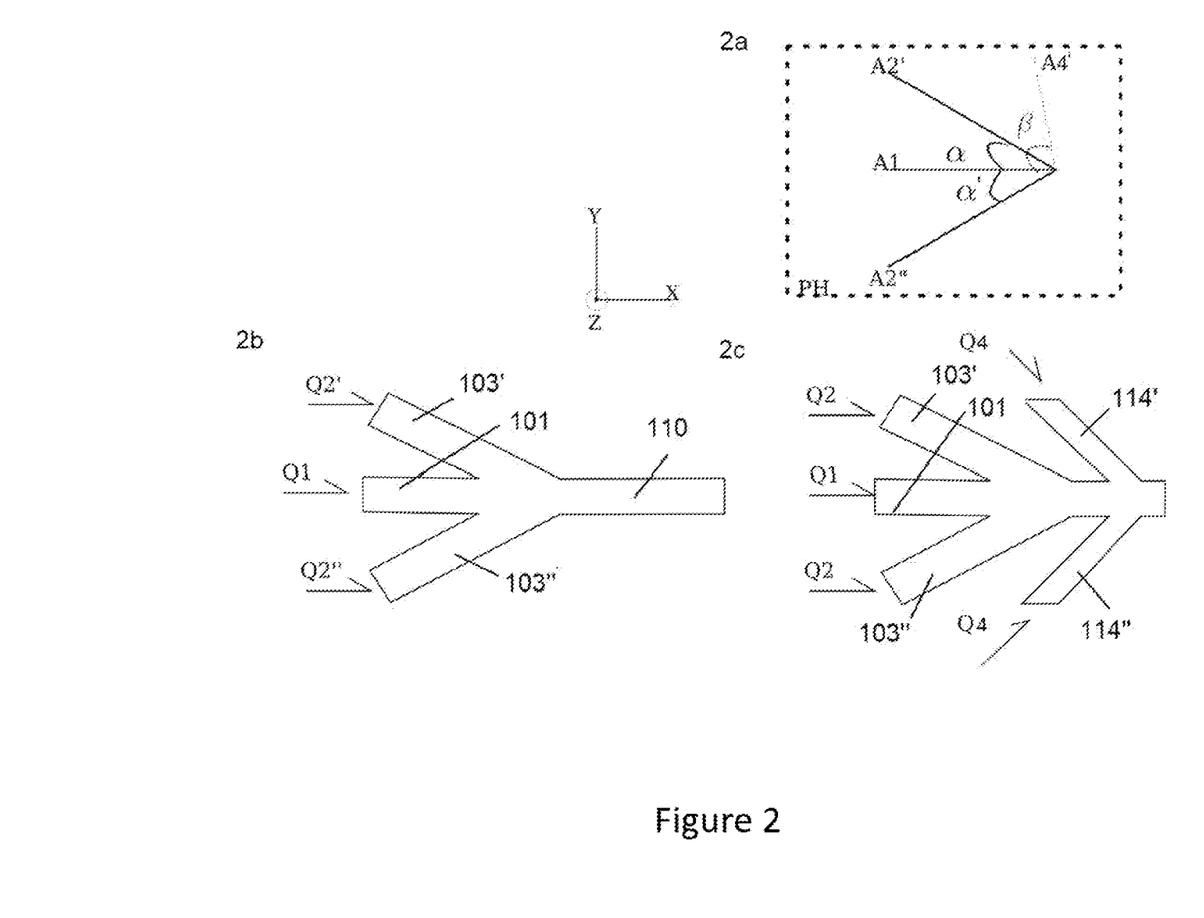
FIG. 2a shows the relative orientation of the axes of the side inlets to the axis of the main inlet of the embodiment shown in FIG. 1.
FIG. 2b shows a top view of a microfluidic device comprising a main inlet and one pair of side inlets.
FIG. 2c shows a top view of a microfluidic device comprising a main inlet and two pairs of side inlets.

FIG. 2a illustrates the relative orientation of axis A1 of the central inlet to axes A2' and A2" of the side inlets of the embodiment shown in FIG. 1.

FIG. 2b shows a top view of a microfluidic device 100 as shown in FIG. 1 comprising a central inlet 101 and a first pair of side inlets 103', 103".

In the embodiment shown in FIG. 1, the axis A1, the axis A2' and the axis A2" are situated in a plane PH. As shown in FIG. 2a, axis A1 and axis A2' define an included angle α. Axis A1 and axis A2" define an included angle α'. Angle α and angle α' are preferably 45 degrees.

The first suspension comprises for example biological cells (first material) in culture medium. The second suspension comprises for example gold nanoparticles (second material) in a biocompatible medium as for example a phosphate buffer.

Optionally, the microfluidic device 100 further comprises a pair of additional inlets 112', 112" for injecting a fluid, to the first junction region 102. The fluid comprises for example distilled water, cell medium or a buffer solution.

The additional inlets 112', 112" are oriented along an additional axis A3 having an orientation different from the orientation of any of the axis A1, A2' and A2". The additional axis A3 of additional side inlet 112 is preferably not oriented in plane PH. In the embodiment shown in FIG. 1, the axis A3 is oriented perpendicular to the plane PH, i.e. in a plane PV. The additional inlet 112' and the additional inlet 112' are preferably injecting the fluid, for example a buffer solution, in opposite directions along axis A3 to the first junction region 102 with a flow rate Q3. By injection a fluid, through additional inlet 112', 112" the symmetry of the microfluidic flow can be influenced. By adjusting the injection of such fluid a rotational symmetry of the outer flow around the central flow can be obtained.

FIG. 2c shows a top view of a microfluidic device similar to the embodiment shown in FIG. 1 and FIG. 2b comprising a central inlet 101 and a first pair of side inlets 103', 103" as well as a second pair of side inlets 114', 114". The first additional inlet 114' is oriented along axis A4' and the second additional inlet 114" is oriented along axis A4". Axis A1 and axis A4' define an included angle β (see FIG. 2a). Similarly, Axis A1 and axis A4" define an included angle β'.

Figure 3:
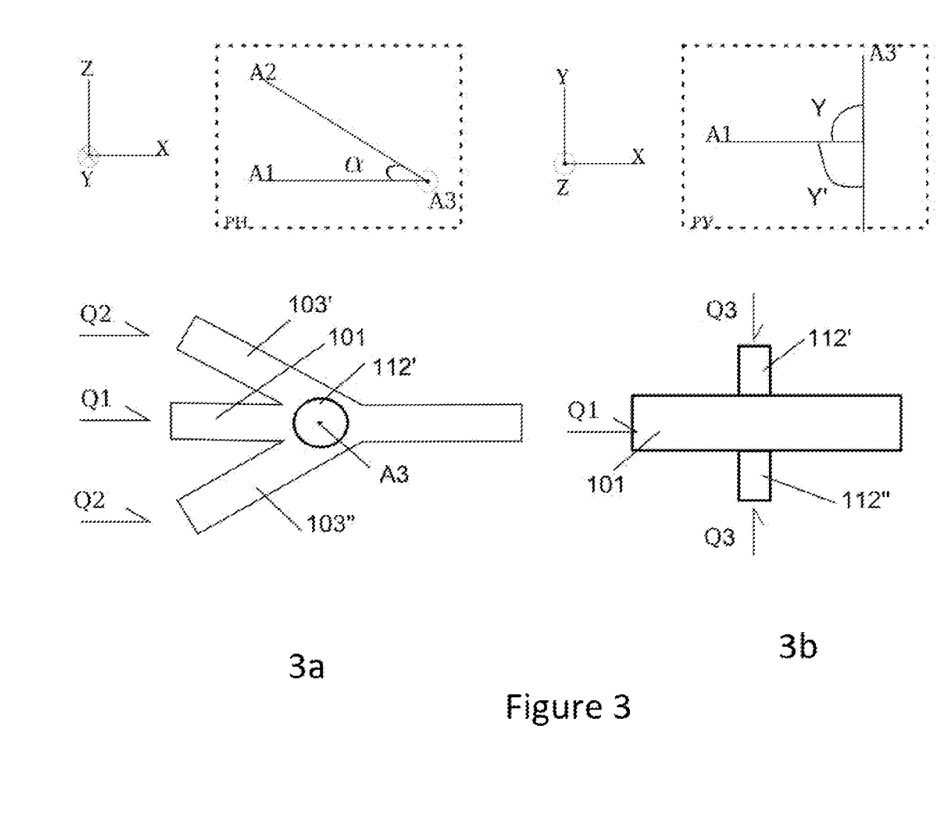
FIGS. 3a and 3b, FIG. 3a and FIG. 3b show respectively a top view and a side view of a microfluidic device comprising a main inlet, a pair of side inlets and a pair of additional inlets.

FIG. 3a and FIG. 3b respectively show a top view and a side view of a microfluidic device comprising a central inlet 101, a first pair of side inlets 103', 103" and a pair of additional inlets 112', 112" oriented along axis A3. The axis A3 is situated in a plane PV. The angle Y (defined as the included angle between A1 and A3 in the plane PV) is preferably ranging from 60 to 90 degrees, for example from 75 to 90 degrees. Most preferably the angle Y is 90 degrees or close to 90 degrees.

Figure 4:
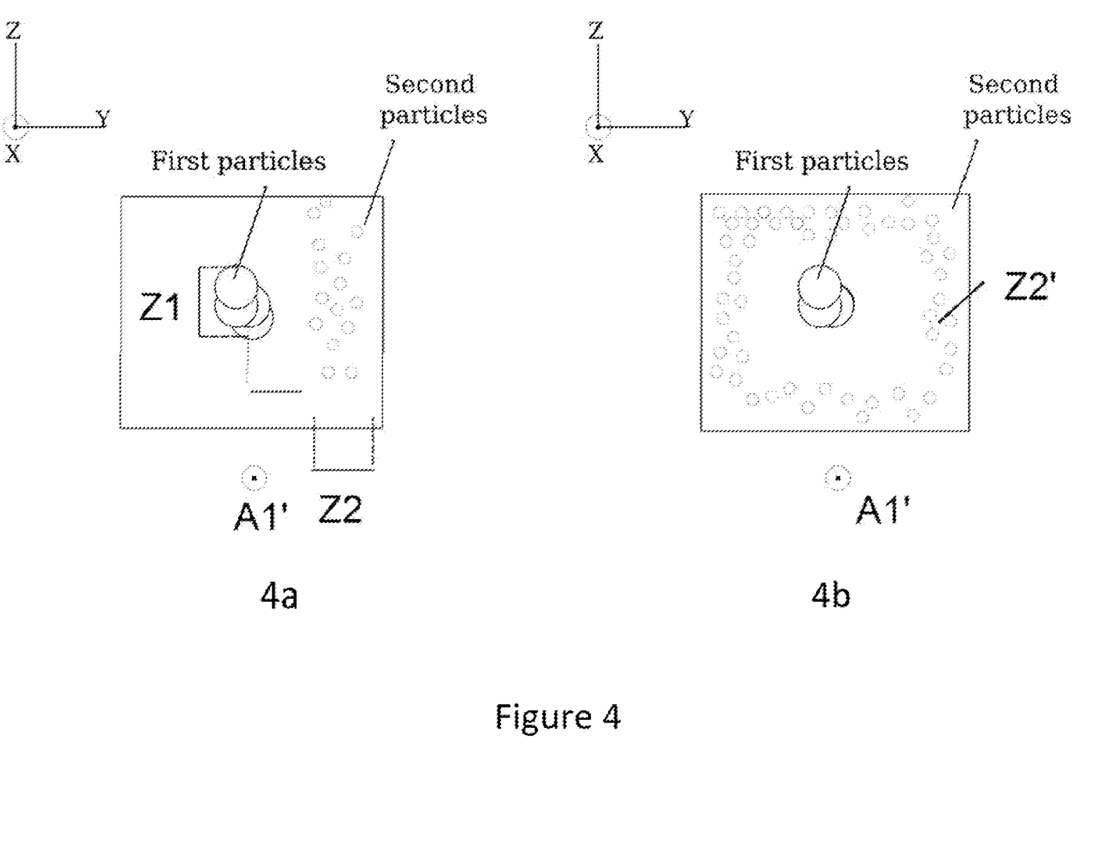
FIGS. 4a and 4b, FIG. 4a and FIG. 4b show two illustrations of a cross-section of a microfluidic flow.

FIG. 4a and FIG. 4b show two illustrations of cross-sections of a microfluidic flow according to the present invention along the outlet axis A1'. FIG. 4a shows a basic organisation of first and second particles obtained by adjusting the flow rates Q1 and Q2. The first particles are organised in zone Z1 and the second particles are organised in zone Z2. By adjusting the flow rates Q1 and Q2 the organisation of the first particles and the second particles in zones Z1 and Z2 and the distance between the first particles and the second particles can be controlled. FIG. 4b shows a cross-section of a microfluidic flow having a preferred organisation of the first and the second particles. The first particles are organised in zone Z1 and the second particles are organised in zone Z2', surrounding the zone Z1. The organisation of the first particles and the second particles in zones Z1 and Z2' and the distance between the first particles and the second particles controlled by adjusting the flow rates Q1, Q2 and Q3.

Figure 5:
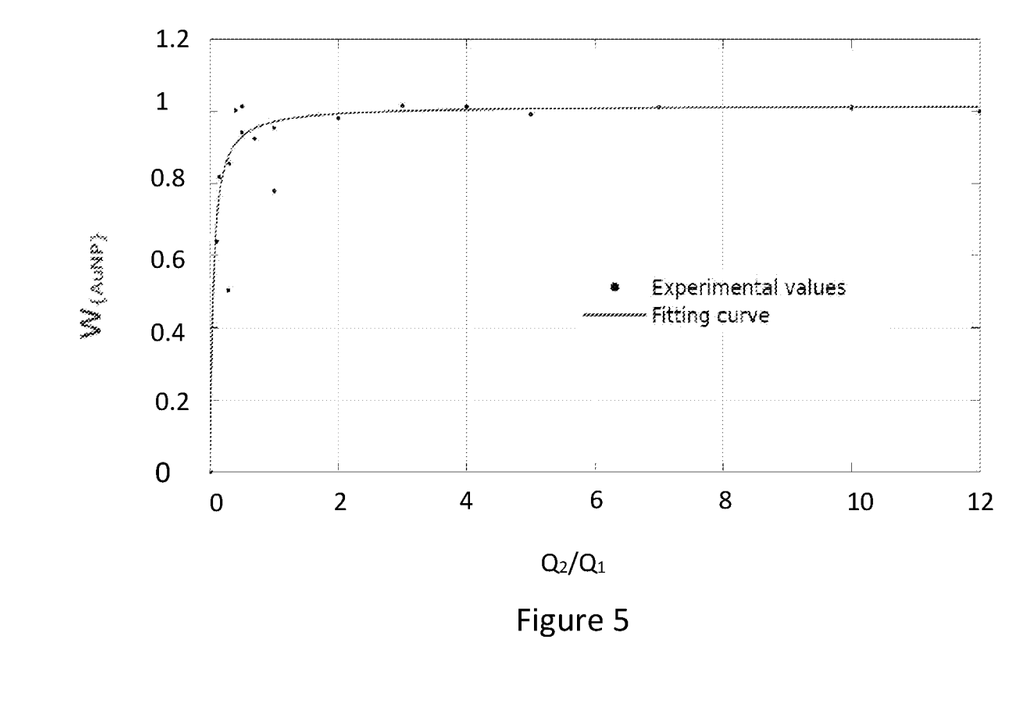
FIG. 5 shows experimental data of the distance between nanoparticles and cells in a microfluidic flow according to the present invention.

FIG. 5 shows experimental data of the distance $W_{(AuNP)}$ between nanoparticles and cells of a microfluidic flow in function of the ratio Q2/Q1. The microfluidic flow comprises a central flow of cells flanked by two outer flows of gold nanoparticles.

The distance W(AuNP) corresponds to $$\frac{W-d}{W}.$$

With w: the radius of the microfluidic channel, and
d: the distance between the gold particles and the cells.

The invention claimed is:

1. A method to provide a microfluidic flow comprising a first material and a second material, said microfluidic flow comprising a central flow and at least one outer flow surrounding or flanking said central flow, said central flow comprising said first material and being substantially free of said second material and said at least one outer flow comprising said second material and being substantially free of said first material, with one of said first material and said second material comprising cells and the other of said first material and said second material comprising solid particles selected from the group of nanoparticles, microparticles and combinations of nanoparticles and/or microparticles, said method comprising the steps of:

providing a first suspension comprising said first material and being free of said second material;

providing a second suspension comprising said second material and being free of said first material;

injecting said first suspension with a first flow rate through a central inlet oriented along a first axis to provide a flow of said first suspension;

injecting said second suspension with a second flow rate to a first junction region of said flow of said first suspension through a first pair of side inlets to provide said microfluidic flow, said first pair of side inlets comprising a first side inlet oriented along a second axis and a second side inlet oriented along a third axis, said first axis and said second axis defining a first included angle and said first axis and said third axis defining a second included angle, said first and second included angles ranging between 10 and 80 degrees, whereby said first flow rate and said second flow rate are adjusted in order to have a ratio of said second flow rate over said first flow rate of at least 4;

optionally injecting a fluid to said microfluidic flow with a third flow rate through at least one additional inlet oriented along a fourth axis, said fourth axis having an orientation different from the orientation of said first axis, said second axis and said third axis.

2. The method according to claim 1, wherein said first material and said second material are not contacting each other in said microfluidic flow.

3. The method according to claim 2, wherein the distance between said cells and said solid particles in said microfluidic flow is at least 0.1 μm.

4. The method according to claim 1, wherein said first included angle and said second included angle range between 30 and 60 degrees and/or wherein said first included angle and said second included angle are of equal magnitude.

5. The method according to claim 1, wherein said first axis, said second axis and said third axis are oriented in a same plane and wherein said fourth axis, if present, is not oriented in said plane.

6. The method according to claim 5, wherein said fourth axis is oriented perpendicular or substantially perpendicular to said plane.

7. The method according to claim 1, wherein said first flow rate ranges between $10^{-7}$ mL/s and 100 mL/s and/or said second flow rate ranges between $10^{-6}$ mL/s and 1000 mL/s.

8. The method according to claim 1, wherein said nanoparticles or said microparticles are selected from the group consisting of metal particles, metal oxide particles or carbon-based particles.

9. The method according to claim 1, wherein the concentration of said cells in said first suspension or said second suspension ranges between $10^2$ and $10^9$ per millilitre and/or wherein the concentration of said nanoparticles and/or said microparticles in said first suspension or said second suspension ranges between 1 nM and 1 μM.

10. The method according to claim 1, wherein said method further comprises the step of injecting said second suspension with a fourth flow rate to the first junction region or to a second junction region through a second pair of side inlets to provide said microfluidic flow, with said second junction region, if present, being positioned downstream said first junction region, said second pair of side inlets comprising a third side inlet oriented along a fifth axis and a fourth side inlet oriented along a sixth axis, said first axis and said fifth axis defining a third included angle and said first axis and said sixth axis defining a fourth included angle, said third and fourth included angles ranging between 10 and 80 degrees.

* * * * *